United States Patent [19]

Ring et al.

[11] Patent Number: 4,917,491
[45] Date of Patent: Apr. 17, 1990

[54] SPECTROMETRY DETECTOR HEAD AND FIBER OPTIC CONNECTOR

[76] Inventors: Lawrence S. Ring, 898 Hillcrest Dr., Laguna Beach, Calif. 92651; Wayne E. Rodgers, 3217 Overbland Ave., Los Angeles, Calif. 90024

[21] Appl. No.: 219,765

[22] Filed: Jul. 15, 1988

[51] Int. Cl.$^4$ .......................... G01N 1/20; G01J 3/00
[52] U.S. Cl. .................................. 356/300; 356/410; 356/436; 356/440; 250/576; 250/227.23
[58] Field of Search ...................... 356/300, 436, 44 D, 356/409, 410, 39, 412; 250/573, 574, 576, 227; 128/633, 634, 636; 422/68; 436/172; 350/96.20, 96.29

[56] References Cited

U.S. PATENT DOCUMENTS 3,740,155 6/1973 Keller et al. .................... 356/409

Primary Examiner—F. L. Evans
Assistant Examiner—Karen Paulette Hantis
Attorney, Agent, or Firm—William H. Pavitt, Jr.; Daniel L. Dawes; Ralf H. Siegemund

[57] ABSTRACT

For use in a spectrophotometry or spectrofluorimetry system, where a fluid to be analyzed, is passed into or through a tube having at least one branch, a plastic device insertable into said branch, said device comprising a tubular plastic member the inner end of which is closed by a transparent transverse end wall, extending into the tube branch and within which an end of a fiber optic cable is removably secured with such end disposed in facing engagement with the inside of said wall, and a detector cap defining a chamber to hold some of the fluid or a dye color reactive to such fluid, is secured on the opposite side of the end wall. The tubular plastic member is removably securable in, and closes the tube branch.

10 Claims, 1 Drawing Sheet

SPECTROMETRY DETECTOR HEAD AND FIBER OPTIC CONNECTOR

FIELD OF THE INVENTION

This invention relates to spectrophotometry systems in general and, specifically, to apparatus for detecting color and fluorescence characteristics, or changes in the color or fluorescence of fluids or dyes, and conveying such color and/or fluorescence characteristics or changes to an analyzer by means of an elongated fiber optic element. When used hereafter the term "color" and "spectrometry" shall be deemed to include fluorescence and index of refraction properties.

BACKGROUND OF THE INVENTION

Spectroscopic analysis of fluids, including gasses, has greatly advanced since its initial experimentation and usage commencing in the 1950's. Among the techniques currently in use has been the passing of a fluid to be analyzed through a tube having at least one branch, and inserting into one of the branches a detecting head which, in essence, is an orificed chamber containing a dye or combination of dyes which react to the fluid content to produce color changes. These color changes are then conveyed by a fiber optic element to a computerized analyzer which produces a digital reading providing intelligence as to the characteristics of the fluid.

A specific application of this technique for blood content analysis is called "optical fluorescence microprocessing". In this procedure, certain specific parameters of interest in blood, such as hydrogen ion, carbon dioxide and oxygen are determined, subjecting a portion of the blood flow to membranes having fluorescent chemicals specific to each such parameter. These chemicals are activated by light arriving through a fiber optic element, such as strands of a cable, to produce fluorescence with a light intensity which will vary depending upon the concentration of the subject parameter being measured. Such variance is picked up by other strands of the fiber optic cable and transmitted back to an analyzer which produces an alpha numeric display reading. Such apparatus may thus produce on line readings of such important parameters in real time and provide such critical information to a cardiovascular or other surgeon and to those assisting him in an operation or other medical procedure.

While this optical fluorescence microsensing technique may be quite effective, heretofore devices used to produce the color response upon exposure to the fluid, have been not only somewhat cumbersome but costly. Prior art systems, such as those made and sold by Cardiovascular Devices, Inc. of Irvine, Calif., have comprised special flow through devices connected by inlet and outlet conduits to provide blood flow and a sensor attachment to the flow through device. However, since both the flow through device and its sensor attachment come into direct contact with the fluid, they must be disposed of after certain uses, and cannot be reused, thereby rendering such detection and analysis procedure quite costly.

SUMMARY OF THE INVENTION

The present invention obviates certain of the problems which have been found to be inherent in currently available detection and analyzing devices, in that the detection head itself, and its mounting, may actually be inserted into a branch of a simple tube, such as a standard Luer fitting tube, and the end of the fiber optic cable which is presented to the dye chamber or the fluid itself to detect color characteristics or changes in the dyes or fluid resulting from exposure to the fluid, may be brought into the tube through the device and presented to the chamber or directly to the fluid in facing engagement therewith, but fully insulated therefrom.

This is accomplished by providing, in effect, a transparent hollow plastic tube which is connectedly insertable into the tube branch. The plastic tube comprises a first inner section, the inner end of which is closed by a transparent tranverse wall. The outer and open end of the first tube section is connected via an intermediate expanding shoulder to a second tube section having an outside diameter closely fitting within the tube to prevent fluid leakage past the said second section, and means are provided removably to secure the tube within the tube branch into which it is inserted. Such means could include a locking sleeve securable to the outer portion of the second tube section, with such sleeve fitting over the tube and adapted to screw tightly over the end of the tube branch. Means may also be provided removably to secure the end of the fiber optic cable, in its desired disposition.

It is a feature of the present invention also to mount on the periphery of the transparent tranverse end wall, an orificed reflective metal cap which defines an open-ended chamber containing a dye or dye combination or fluid, and which chamber is closed upon attachment to the transverse end wall. Such cap mounting may be accomplished by providing projections extending axially from the cap, and recesses about the periphery of the transparent transverse end wall to receive such projections. However, in some applications, such as for refractive indexing, such an orificed metal cap, and the chamber which it defines, may be dispensed with altogether, so that the transparent transverse wall, or any other transparent closure in proper alignment with the end of the fiber optic cable may be disposed in direct contact with the fluid in the tube, the refractive index or other parameter of which fluid is it to be determined.

The device of the present invention may be manufactured at relatively low cost in comparison with devices heretofore available for accomplishing the monitoring of fluid or exposure of dyes to fluid contained in a tube, and bringing the end of a fiber optic cable to a position where color characteristics or changes may be transmitted through the fiber optic cable to a spectrometry analyzer. This greatly reduces the cost and improves the accuracy of such procedures where, after each spectrometry analysis, all parts of a detector device which come into contact with the fluid being analyzed or monitored must be disposed of.

BRIEF DESCRIPTION OF THE DRAWINGS

In the accompanying drawing.

DESCRIPTION OF THE PREFERRED EMBODIMENT

Figure 1:
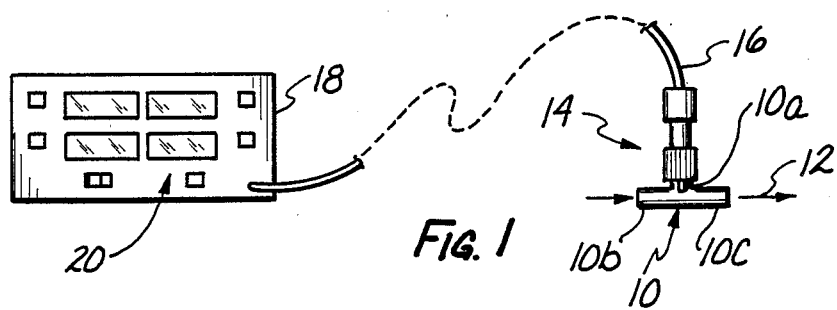
FIG. 1 is a schematic of a colorimetry/fluorimetry system in which the present invention may be utilized.

For an understanding of how the device of the present invention may be employed in a colorimetry/fluorimetry system, reference should be made to FIG. 1 where 10 represents a Luer tube having a branch 10a extending perpendicularly from the aligned flow-through sections 10b, 10c. A fluid 12 which, of course, may include a gas, enters through the section 10b and exits out through the section 10c. As the fluid 12 passes the branch 10a, some of the fluid would tend to enter and pass out through the branch 10a. Such passage into and out of branch 10a is prevented, however, by the insertion into the branch 10a of the detection and fiber optic cable connector device 14, the details of which will be more fully described hereinafter. Extending out of the device 14, is a fiber optic cable 16, which is connected to, and enters the analyzer 18, having a digital reading face 20.

Figure 2:
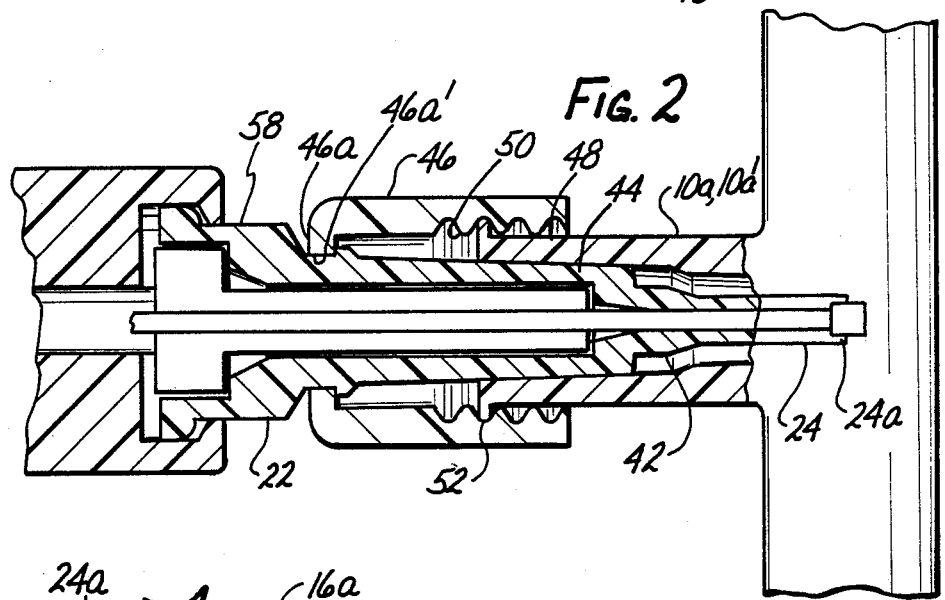
FIG. 2 is a section greatly expanded in size, illustrating the device of the present invention inserted in a luer tube.
Figure 3:
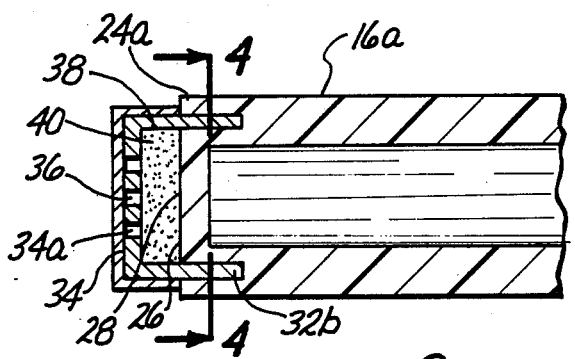
FIG. 3 is a detailed section of the end of the tubular insert shown in FIG. 2.
Figure 4:
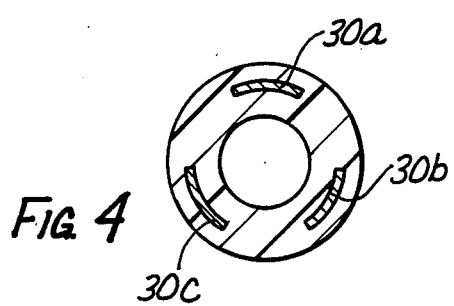
FIG. 4 is a section taken on the line 4—4 of FIG. 3.

Turning next to FIG. 2 of the drawing, the device of the present invention comprises a plastic tubular insert 22 which is inserted into the branch 10a of the Luer tube. This tubular insert comprises an inner section 24 which is closed at its inner end 24a by a transparent transverse wall 26. As may be seen from FIGS. 3 and 4, the periphery of the transparent transverse wall 26 is recessed in three places 30a, 30b and 30c. The purpose of these recesses 30a, 30b and 30c is to receive the projections 32a, 32b and 32c, respectively, which extend from the rim of the small cylindrical cap 34. This cylindrical cap 34 is preferably made of a stainless steel which is inwardly reflective or may be provided with an inner reflective coating and is finely orificed on its end wall or side walls 36. The cap 34 defines an open-ended chamber 38 into which a small quantity of dye or combination of dyes may be placed, or into which the fluid 12 will pass for analysis. The chamber 38 is closed by attachment of the cap 34 to the wall 26 by the insertion of the axial projections 32a, 32b and 32c into the recesses 30a, 30b and 30c, respectively.

On the opposite side of the transparent transverse wall, the end 16a of the fiber optic cable 16, is brought into facing engagement with the wall 26, so that the color of the dye or combination of dyes 40, or color of solution in the chamber 38, or changes in such color, may be picked up by the fiber optic cable 16 for conveyance to the analyzer 18. Index matching fluid may be used to minimize internal reflections.

It will be noted from FIG. 2 that the tubular insert 22, in addition to being comprised of the inner section 24, has an intermediate section 42 of increasing outside diameter, and an outer section 44 of an outside diameter which fits closely within the Luer tube branch 10a. Thereby, any fluid 12 which enters the luer tube branch 10a, and passes around the inner section 24 of the tubular insert 22 is blocked from passing out of the branch 10a.

The tubular insert 22 may be secured within the branch 10a by means of a standard Luer cap which comprises a sleeve-like member 46. This member desirably has an inside diameter slightly greater than the outside diameter of the Luer tube branch 10a, the edge of the outer end 10a' of which may be provided with a slight projection 48. The inner wall 50 of the member 46 may be threaded, so that the member 46 may be screwed onto the end 10a' of the branch 10a. An annular bead 52 may be provided around the outer section 44 of the tubular insert 22. The opposite end of the sleeve-like locking member 46 is partially closed by a wall 46a having a circular opening 46a', just slightly less than the the outside diameter of the bead 52, so that the sleeve-like locking member 46 may be snapped over the bead 52, thereby preventing the member 46 from sliding axially off the outer section 44, the intermediate section 42 and the inner section 44. In order to prevent the member 46 from sliding off the opposite end 44a of the outer section 44, the latter desirably has an annular stop portion 58 of greater diameter than that of the circular opening 46a'.

In use, it may be seen, then, that, a fiber optic cable 16 may be inserted into the tubular insert 22, to where its end 16a is disposed against the transparent transverse wall 26. The other end of the fiber optic cable extends into the analyzer 18. The tubular insert 22 is then inserted into the end 10a' of the branch 10a of the Luer tube 10, and secured thereto, by threading the sleeve-like locking member 46 over the projection 10a on the end 10a' of the Luer tube. Desirably, in some applications, the capped end of inner section 24 of the tubular insert 22 will actually project into the flow path through sections 10b, 10c.

As fluid is passed through the tube sections 10b, 10c, some of the fluid 12 comes into direct contact with the orificed cylindrical cap 34, and passes through the orifices 34a and into contact with the dye 40 or into the measurement zone. Any color change in the chamber 38 is conveyed through the transparent transverse wall 26 to the fiber optic end 16a, with the aid of the reflective coating or surface 28, with the result that such light or color change is further conveyed by the fiber optic cable 16 to the analyzer 18 to produce a digital reading on the face 20.

Upon completion of the analysis of the fluid in the tube 10, the device 14 is withdrawn from branch 10a, the end 16a of the fiber optic cable 16 is pulled out of the element 22, and the latter is discarded. When the next fluid 12 is to be analyzed, a new tube 10 and connecting hose are provided for the fluid flow, the end 16a of the fiber optic element is reinserted into the tubular element 22 of a new device 14, and the procedure described above is repeated.

Alternatively, the devices may be installed at multiple locations and left in place while either or both the fiber optic cable 16 and analyzer 18 may be moved from one location to the next.

Because the device 14 may be produced at a much lesser cost than devices currently being used for analysis for fluids passing through tubes, and because of the ease with which a fiber optic element 16 may be inserted into the tubular element 22, and the latter inserted into a luer tube branch 10a, and removably secured therein by the sleeve-like locking member 46, it will be apparent that the cost of conducting spectro-analytic procedures may be considerably reduced over the cost of such procedures as heretofore conducted with current state of the art equipment.

We claim:

1. For use in fiber optic spectrophotometry and/or spectrofluorimetry systems in which a sensing head is inserted in a branch of a tube containing a fluid for exposure to said fluid, and color characteristics of the fluid or a dye in contact with the fluid are sensed by the head and conveyed through an elongated fiber optic cable to a chemical analyzer, a connector device including a sensing head and disposing an end of the fiber optic cable in light transmitting proximity to, but insulated from the fluid, said device comprising:
- (A) a tubular member, said member having an outside diameter less than the inside diameter of the tube branch into which the member is to be inserted, said tubular member being open at its outer end and closed at its inner insertable end by an optically transparent tranverse wall, said tubular member having an inside diameter greater than the outside diameter of the end of the elongated fiber optic cable to receive and removably secure the last said end for disposition in facing engagement with said transverse wall;
- (B) means to retain the closed end of said tubular member upon its insertion within the tube branch to effect contact with the fluid therein and to prevent fluid from passing by the tubular member and out of the said tube branch;
- (C) an orificed cap defining an open chamber; and
- (D) means to attach said cap onto the periphery of the transparent transverse wall so that said chamber is closed by the last said wall thereby exposing the color of the chamber contents and its changes to the end of the fiber optic cable through said transparent wall.

2. The device as described in claim 1 wherein said chamber contains a dye reactive to one or more parameters of the fluid in the tube branch.

3. The device as described in claim 1 wherein said cap is cylindrical and has an open end and the other end is closed by a tranverse wall.

4. The device as described in claim 1 wherein the means to retain the end portion of the tubular member within the tube branch comprises an outer hollow tube section connected to and extending from the open end of the tubular member by an intermediate shoulder section increasing its outside diameter to the point where at least a portion of said shoulder section fits closely within the end of the tube branch, said outer tube section having an inside diameter at least as great as the inside diameter of the tube branch.

5. The device as described in claim 4 wherein the tube branch has a luer taper.

6. The device as described in claim 3 wherein the periphery of the end wall closing the end of the hollow tube is recessed and the cap is provided with at least one axially extending element adapted to seat in said recess, thereby to enable said cap to be secured in proximity to said transparent transverse wall.

7. The device as described in claim 1 wherein the orificed cap is provided with an inwardly reflecting surface.

8. The device as described in claim 4 wherein said outer tube has an annular bead on its outside surface and a radially expanded section at its outside end, and a resilient locking sleeve is provided, said locking sleeve having a first open end with an inside diameter slightly greater than the outside diameter of the tube branch to fit closely thereover, and a second open end having a radially inwardly projecting annulus with an inside diameter to snap over said bead, the inside wall of said sleeve being threaded to enable said sleeve to be screwed onto any tube branch having a mating end or threading.

9. For use in fiber optic spectrophotometry and/or spectrofluorimetry systems in which a sensing head is inserted in a branch of a tube containing a fluid for exposure to said fluid, and color characteristics of the fluid are sensed by the head and conveyed through an elongated fiber optic cable to a chemical analyzer, a connector device including a sensing head and disposing an end of the fiber optic cable in light transmitting proximity to, but insulated from the fluid, said device comprising:
- (A) a tubular member, said member having an outside diameter less than the inside diameter of the tube branch into which the member is to be inserted, said tubular member being open at its outer end and closed at its inner insertable end by an optically transparent closure, said tubular member having an inside diameter greater than the outside diameter of the end of the elongated fiber optic cable to receive and removably secure the last said end for disposition in facing engagement with said transparent closure; and
- (B) means to retain the closed end of said tubular member upon its insertion within the tube branch to effect contact with the fluid therein and to prevent fluid from passing by the tubular member and out of the said tube branch.

10. The device as described in claim 9 wherein means are provided to retain the end of the fiber optic cable within the tubular member in facing engagement with the transparent closure.

* * * * *